(12) United States Patent
Suzuki et al.

(10) Patent No.: US 6,849,059 B2
(45) Date of Patent: Feb. 1, 2005

(54) IRRIGATION/ASPIRATION APPARATUS

(75) Inventors: Nobuo Suzuki, Nukata-gun (JP); Hideo Oda, Gamagori (JP)

(73) Assignee: Nidek Co., Ltd. (JP)

( * ) Notice: Subject to any disclaimer, the term of this patent is extended or adjusted under 35 U.S.C. 154(b) by 163 days.

(21) Appl. No.: 10/349,093

(22) Filed: Jan. 23, 2003

(65) Prior Publication Data

US 2003/0146299 A1 Aug. 7, 2003

(30) Foreign Application Priority Data

Jan. 23, 2002 (JP) ......................................... 2002-014776

(51) Int. Cl.[7] ................................................ A61M 1/00
(52) U.S. Cl. ............................. 604/31; 604/35; 604/67; 604/151
(58) Field of Search ............................. 604/31, 35, 45, 604/67, 132, 133, 140, 141, 151

(56) References Cited

U.S. PATENT DOCUMENTS 3,812,855 A * 5/1974 Banko ........................ 604/31
4,227,420 A 10/1980 Lamadrid
6,491,661 B1 * 12/2002 Boukhny et al. ............. 604/67
6,723,065 B2 * 4/2004 Kishimoto .................... 604/43

FOREIGN PATENT DOCUMENTS

JP    11-332904 A1    12/1999

* cited by examiner

Primary Examiner—Gene Mancene
Assistant Examiner—Patrick Buechner
(74) Attorney, Agent, or Firm—Rader, Fishman & Grauer PLLC

(57) ABSTRACT

An irrigation/aspiration apparatus capable of detecting an aspiration pressure accurately while preventing an aspirated liquid from entering an aspiration pressure detecting system. The apparatus, which supplies an irrigation liquid to a surgical site and aspirates the supplied liquid with eliminated tissue to be discharged out of a body, has an aspiration channel, a shape-alterable diaphragm in pouch form, including a liquid chamber which communicates with the aspiration channel, a gas chamber which stores and surrounds the diaphragm, and a pressure sensor connecting with the gas chamber via a connecting part.

8 Claims, 8 Drawing Sheets

IRRIGATION/ASPIRATION APPARATUS

BACKGROUND OF THE INVENTION

1. Field of the Invention

The present invention relates to an irrigation/aspiration apparatus which supplies an irrigation liquid (fluid) to a surgical site and aspirates the supplied liquid with eliminated tissue.

2. Description of Related Art

A conventional irrigation/aspiration apparatus is known which supplies (infuses) an irrigation liquid to a surgical site (a diseased part), and also aspirates and removes the supplied liquid with tissue eliminated from the surgical site. Particularly in the field of ophthalmology, the apparatus is used in cataract surgery, vitreos surgery and the like. In the cataract surgery, the apparatus aspirates eliminated tissue together with an irrigation liquid supplied to a surgical site of a patient's eye using a handpiece with a chip having an aspiration hole mounted on its tip, and discharges the aspirated liquid with the eliminated tissue from one end of an aspiration tube.

Incidentally, this kind of apparatus must have a system for controlling aspiration pressure during surgery. Therefore, an apparatus is well known in which an aspiration pressure detecting system having a pressure sensor and a connecting part are provided midway along the aspiration tube and in which the pressure sensor detects the aspiration pressure via the connecting part. However, since the pressure sensor detects the aspiration pressure in the aspiration tube directly, the liquid with the eliminated tissue aspirated from the patient's eye sometimes enters the aspiration pressure detecting system. When the aspirated liquid enters the aspiration pressure detecting system, bacteria propagate there, and it is not free from the possibility that the liquid including the bacteria flows back into the aspiration tube and causes in-hospital infection during the surgery. As a remedy for that, a method is applied where a disposable filter and the like are attached to the connecting part between the pressure sensor and the aspiration tube, so that the bacteria are prevented from moving.

However, the method of attaching the filter and the like to the connecting part makes it difficult to detect the aspiration pressure accurately because of resistance of the filter, and clogging caused by the tissue and other objects which are adhered to the filter.

In addition, at the time of detaching the aspiration tube from the apparatus, the liquid with the eliminated tissue aspirated from the patient's eye might flow outs and the apparatus and its periphery possibly become dirty.

SUMMARY OF THE INVENTION

An object of the invention is to overcome the problems described above and to provide an irrigation/aspiration apparatus capable of detecting an aspiration pressure accurately while preventing an aspirated liquid from entering an aspiration pressure detecting system.

To achieve the objects and in accordance with the purpose of the present invention, an irrigation/aspiration apparatus has an aspiration channel, a shape-alterable diaphragm in pouch form, including a liquid chamber which communicates with the aspiration channel, a gas chamber which stores and surrounds the diaphragm, and a pressure sensor connecting with the gas chamber via a connecting part.

In another aspect of the present invention, an irrigation/aspiration apparatus has an aspiration channel, a shape-alterable diaphragm in pouch form, including a liquid chamber which communicates with the aspiration channel, a gas chamber which stores and surrounds the diaphragm, and a pressure sensor connecting with the gas chamber via a connecting part. A rib is provided on at least one of an inside wall and an outside wall of the diaphragm.

Additional objects and advantages of the invention are set forth in the description which follows, are obvious from the description, or may be learned by practicing the invention. The objects and advantages of the invention may be realized and attained by the irrigation/aspiration apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
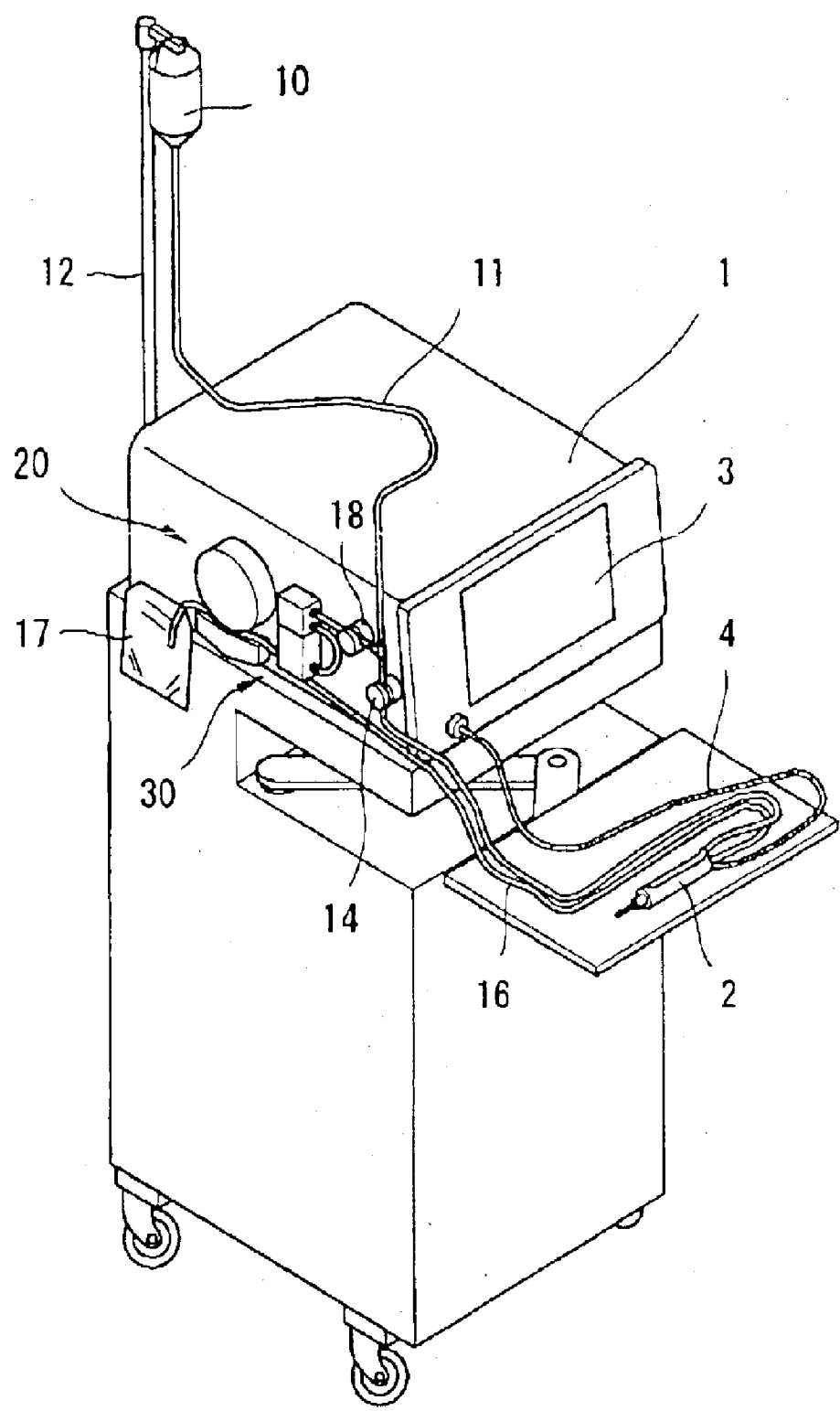
FIG. 1 is a schematic external view of an irrigation/aspiration apparatus.
Figure 2:
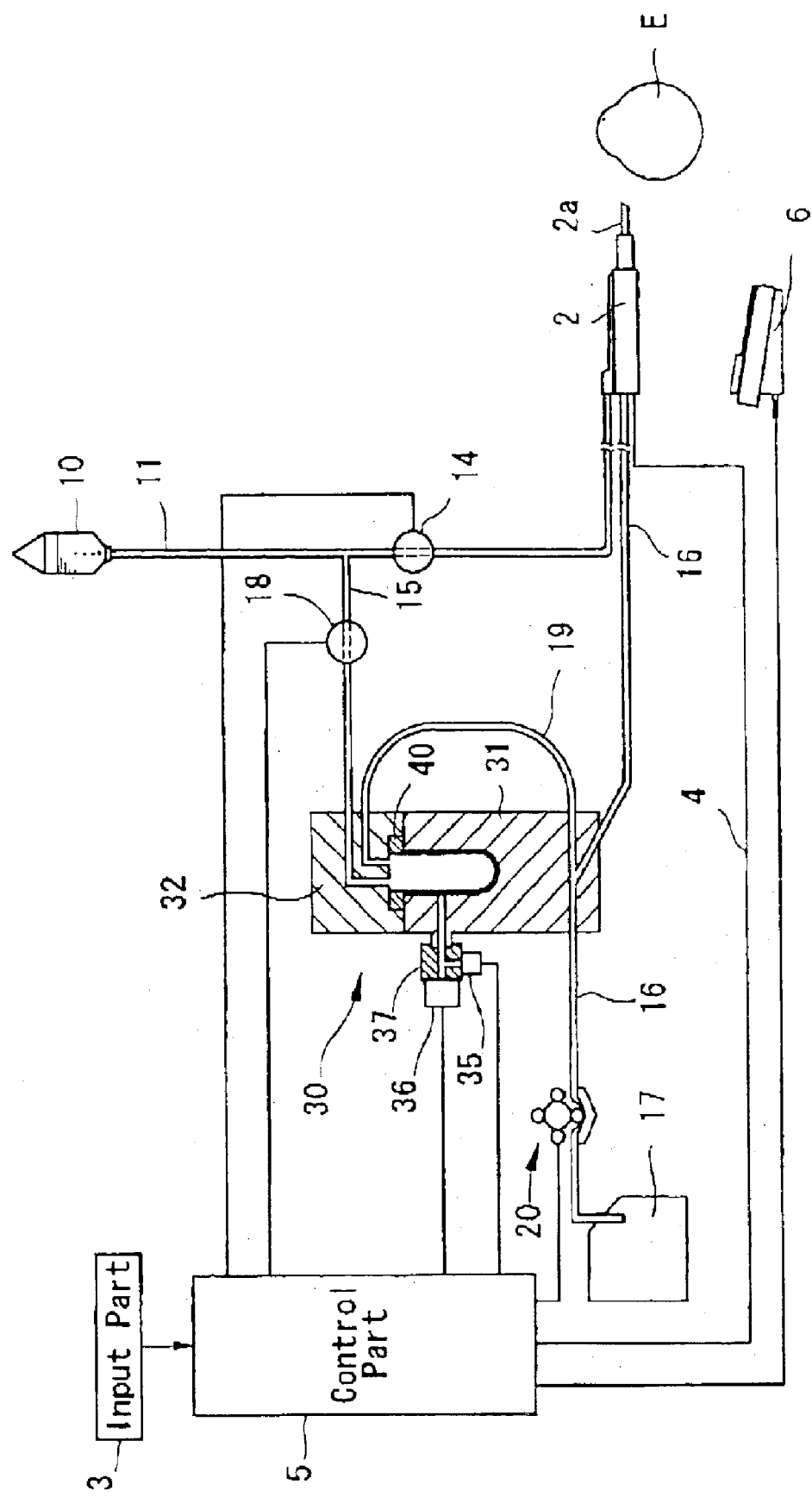
FIG. 2 is a view showing a schematic configuration of a primary part of the apparatus.

A detailed description of one preferred embodiment of an irrigation/aspiration apparatus embodied by the present invention is provided below with reference to the accompanying drawings. FIG. 1 is a schematic external view of an irrigation/aspiration apparatus consistent with the preferred embodiment. FIG. 2 shows a schematic configuration of a primary part of the apparatus.

Reference numeral 1 denotes a main body of the apparatus. A surgeon grasps a US handpiece 2. A cylindrical chip 2a for fragmentation with an aspiration hole is attached to the tip of the handpiece 2. The chip 2a is subjected to ultrasonic vibrations to perform fragmentation and emulsification of nucleus of a crystalline lens. An input part 3 serves as an operation panel for setting various matters (surgical conditions) such as irrigation pressure and aspiration pressure. A cable 4 supplies power to the handpiece 2 in order to induce ultrasonic vibrations in the chip 2a. The main body 1 stores a control part 5 for controlling the entire apparatus.

An irrigation bottle 10 contains an irrigation liquid such as a saline which is supplied to a patient's eye E. An irrigation tube 11 leads the irrigation liquid to the eye E via the handpiece 2. A pole 12 hangs the bottle 10, and moves up and down. The bottle 10 may thereby change its height. The bottle 10 is arranged at such a height as to keep a pressure inside the eye E properly.

A control valve 14 is provided midway along the irrigation tube 11, and is opened and closed to control flow of the irrigation liquid. One end of the irrigation tube 11 is connected with the bottle 10, and the other end is connected with the handpiece 2. The US handpiece 2 is changed for any of various kinds of handpieces including that for irrigation/aspiration according to a step in surgery, a method of surgery or the like, and the changed handpiece is connected and may be replaced with another before being used.

A flexible aspiration tube 16 is used for discharging tissue such as nucleus subjected to fragmentation and emulsification together with the irrigation liquid aspirated through the aspiration hole of the chip 2a out of the body. In a rear direction midway along the aspiration tube 16, a peristaltic aspiration pump 20 is provided in order to generate aspiration pressure in the aspiration tube 16. The control part 5 controls rotation of the pump 20 to adjust the aspiration flow rate inside the aspiration tube 16. The aspirated liquid with the tissue is discharged and flushed into a drainage bag 17.

A tube 19 is branched off from the aspiration tube 16. One end of the tube 19 is connected midway along the aspiration tube 16, and the other end of that is connected with a pressure-changing unit 30. The unit 30 will be described in detail later. The unit 30 may be desirably connected with, and disconnected from the main body 1 through a pressure sensor 36 and a connecting part 37 which are provided on the main body 1 and constitute an aspiration pressure detecting system.

Further, a tube 15 is branched off from the irrigation tube 11 between the bottle 10 and the valve 14. The tube 15 is also connected with the unit 30, and a vent valve 18 is provided midway along the tube 15.

The control part 5 drives and controls the apparatus in accordance with a signal indicative of a foot position when a footswitch 6 is depressed. For example, when the US handpiece 2 is used, there are three foot positions which are indicative of an irrigation mode for performing only irrigation, an irrigation/aspiration mode for performing irrigation and aspiration, and an irrigation/aspiration/fragmentation mode for performing irrigation, aspiration and ultrasonic fragmentation and emulsification, respectively.

Figure 3:
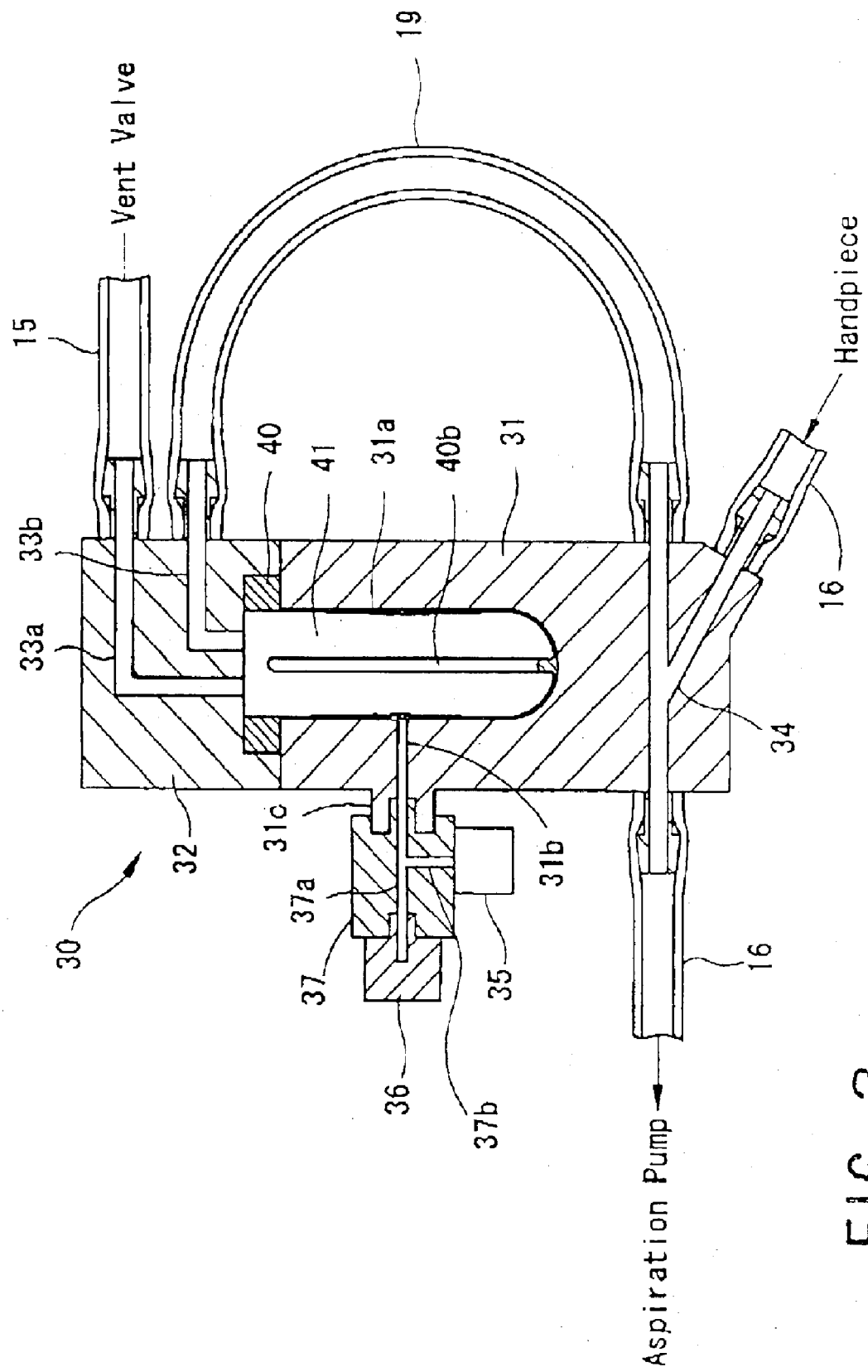
FIG. 3 is a sectional view showing a configuration of an aspiration pressure detecting system of the apparatus.
Figure 4:
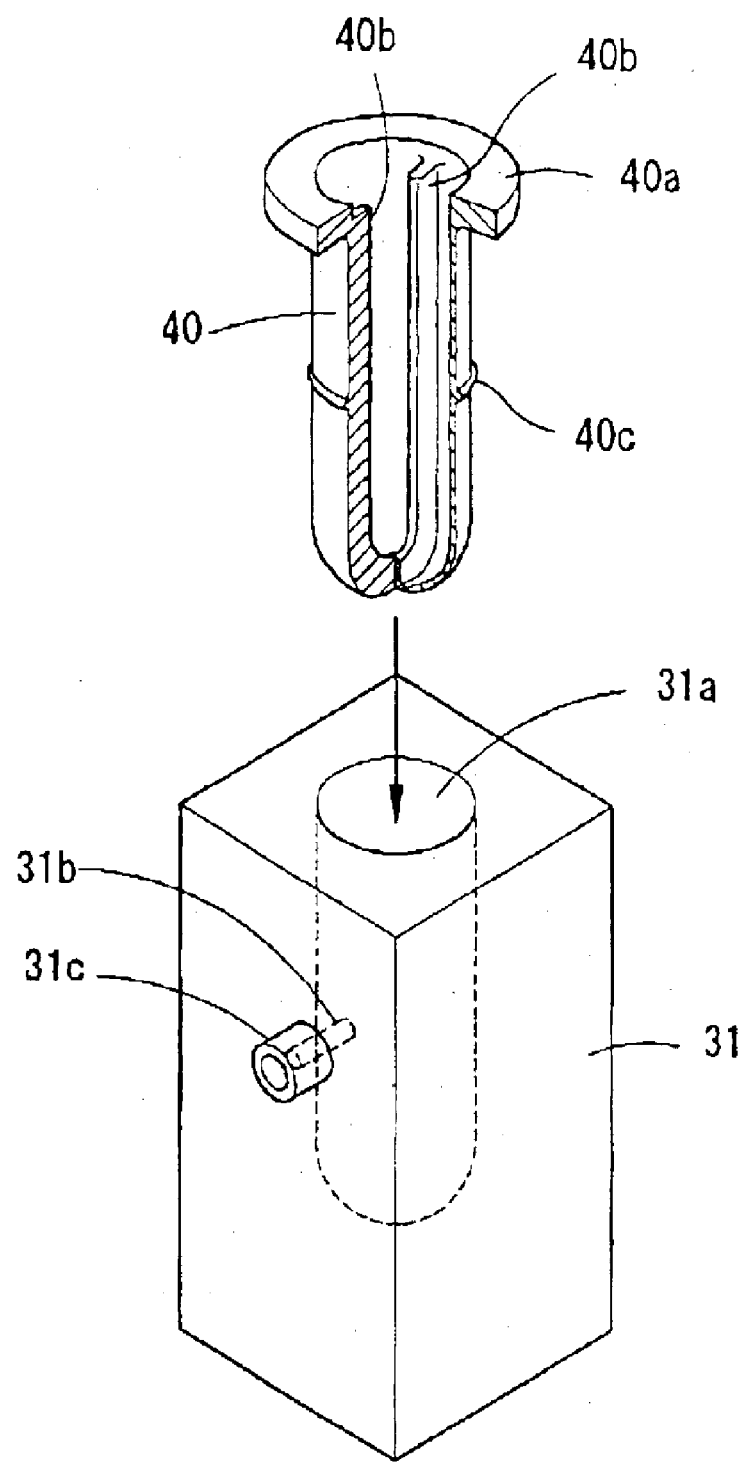
FIG. 4 is a view showing a configuration of a diaphragm and a chamber.

Next, a configuration of the unit 30 will be described based on FIGS. 3 and 4. The unit 30 includes a diaphragm 40 in slim-pouch form, a lower case 31 with a gas chamber 31a which stores the diaphragm 40, and an upper case 32 which covers the diaphragm 40 stored in the lower case 31. A channel 33a connected with the tube 15 and a channel 33b connected with the tube 19 are formed in the upper case 32. The openings of the channels 33a and 33b communicate with a liquid chamber 41 formed by the diaphragm 40.

The diaphragm 40 consistent with the preferred embodiment has a cylindrical shape with a round tip, and a flange 40a is formed at an opening of the diaphragm 40 in order to ensure airtightness. The diaphragm 40 is made of flexible silicon, and thickness of its sidewall is 0.1 to 0.2 mm. Thus, the diaphragm 40 is arranged to alter (transform) its shape smoothly in accordance with internal pressure. In addition, a rib (convex part) 40b having thickness is formed on an inside wall of the diaphragm 40 to extend from the flange 40a to the round tip (in a direction of a depth of the diaphragm 40). When the diaphragm 40 is stored in the chamber 31a inside the lower case 31, the upper case 32 holds the flange 40a in order that the diaphragm 40 is fixed and sealed.

Further, a rib (convex part) 40c which extends in a direction of the circumference of the cylindrical part is formed around an outside wall of the diaphragm 40. A gas line 31b which communicates with the chamber 31a and the pressure sensor 36 are formed in the lower case 31, and the rib 40c is provided at such a position as to fall at the opening of the gas line 31b when the diaphragm 40 is stored in the chamber 31a.

A mounting part 31c formed on the lower case 31 is connected with the connecting part 37 fixed on the main body 1, and the gas line 31b which communicates with the chamber 31a is connected with a gas line 37a formed in the connecting part 37. The pressure sensor 36 is attached to the tip of the gas line 37a. The pressure sensor 36 detects gas pressure inside a channel from the chamber 31a to the gas line 37a, thereby detecting liquid pressure varying inside the diaphragm 40, in other words, detecting aspiration pressure. In addition, a gas line 37b branched off from the gas line 37a is connected with an electromagnetic valve 35, and the valve 35 is opened and closed to perform discharge of air and sealing.

Incidentally, a bifurcating channel 34 is formed in the lower case 31 and connects the tube 19 with a midway along the aspiration tube 16.

The followings are descriptions about operations of the apparatus provided with the aforementioned configuration. On the occasion of surgery, the height of the bottle 10 is adjusted, the respective tubes and others are attached to the handpiece 2, the pump 20, or the unit 30, and other necessary preparations are made. Additionally, the mounting part 31c is inserted in the connecting part 37. Upon completion of installing the tubes and others, the tubes are filled with the irrigation liquid. For that purpose, firstly, the tip of the handpiece 2 (chip 2a) is capped so as not to leak the irrigation liquid, and a test switch on the input part 3 is depressed. Once the test switch has been depressed, the control part 5 tightens the valve 18, opens the valve 14 and drives the pump 20. According to these operations, an aspiration channel of the handpiece 2 and the aspiration tube 16 are deprived of air and filled with the irrigation liquid.

Once the aspiration tube 16 has been filled with the irrigation liquid (this is detected based on a signal output from the pressure sensor 36), the control part 5 tightens the valve 14 and opens the valve 18. By these operations, the irrigation liquid from the bottle 10 is led to the unit 30, and the chamber 41 inside the diaphragm 40 and the tube 19 are deprived of air and filled with the irrigation liquid. At this time, the control part 5 opens the valve 35, so that air inside a space from the chamber 31a to the gas line 37a has atmospheric pressure. Once the handpiece 2, the respective tubes and the diaphragm 40 (chamber 41) have been filled with the irrigation liquid, the control part 5 stops the pump 20 and tightens the valves 14, 18 and 35.

Once the apparatus has gone through the necessary settings, the surgeon inserts the chip 2a attached to the handpiece 2 into the eye E, depresses the footswitch 6, and performs surgery under phacoemulsification while controlling operations of supplying the irrigation liquid, aspirating and giving ultrasonic vibrations. When the signal for aspiration from the footswitch 6 is input, the control part 5 drives the pump 20. The pump 20 generates aspiration pressure, and the pressure travels through the aspiration tube 16 to the handpiece 2, then the irrigation liquid inside the eye E is aspirated through the aspiration hole of the chip 2a.

Figure 5:
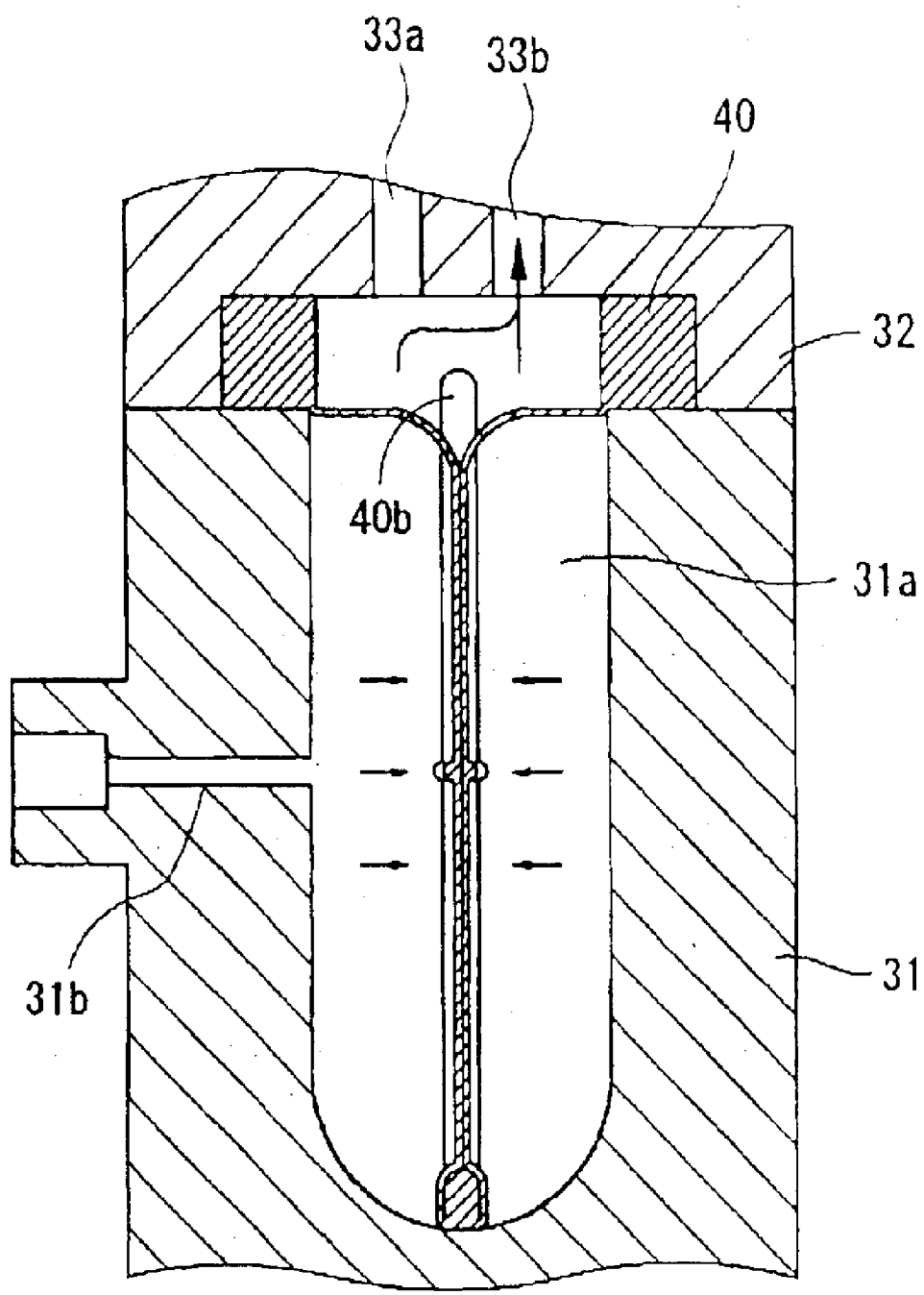
FIG. 5 is a sectional view of the diaphragm and the chamber.

The aspiration pressure generated inside the aspiration tube 16 is converted to gas pressure using the unit 30, and the pressure sensor 36 detects the gas pressure. If the aspiration pressure increases by rotation of the pump 20, the irrigation liquid inside the diaphragm 40 is aspirated via the tube 19. Further, if the aspiration pressure increases by blocking the chip 2a and for other reasons, the diaphragm 40 shrinks as shown in FIG. 5. At this moment, the thick rib 40b provided inside the diaphragm 40 does not alter its shape, and only a sidewall made of thin membrane shrinks when the diaphragm 40 alters its shape. Therefore, negative pressure is applied inside the diaphragm 40, and the rib 40b acts as a guide for steadying the shape-alteration so that only the sidewall made of thin membrane alters its shape. Because of the rib 40b, the diaphragm 40 alters its shape without curling altogether, so that it may recover its original state when the negative pressure decreases therein. Furthermore, the rib 40b also acts as a prevention of a mid-block formed of air remained on the tip side of the diaphragm 40 (the lower part shown in FIGS. 5 and 6) because of an intimate contact of the inner part through the process of the shape-alteration. The diaphragm 40 shrinks, and the gas pressure in the space from the chamber 31a to the gas line 37a is thereby subjected to negative pressure. Therefore, the pressure sensor 36 connecting with the gas line 37a may detect the aspiration pressure.

Figure 6:
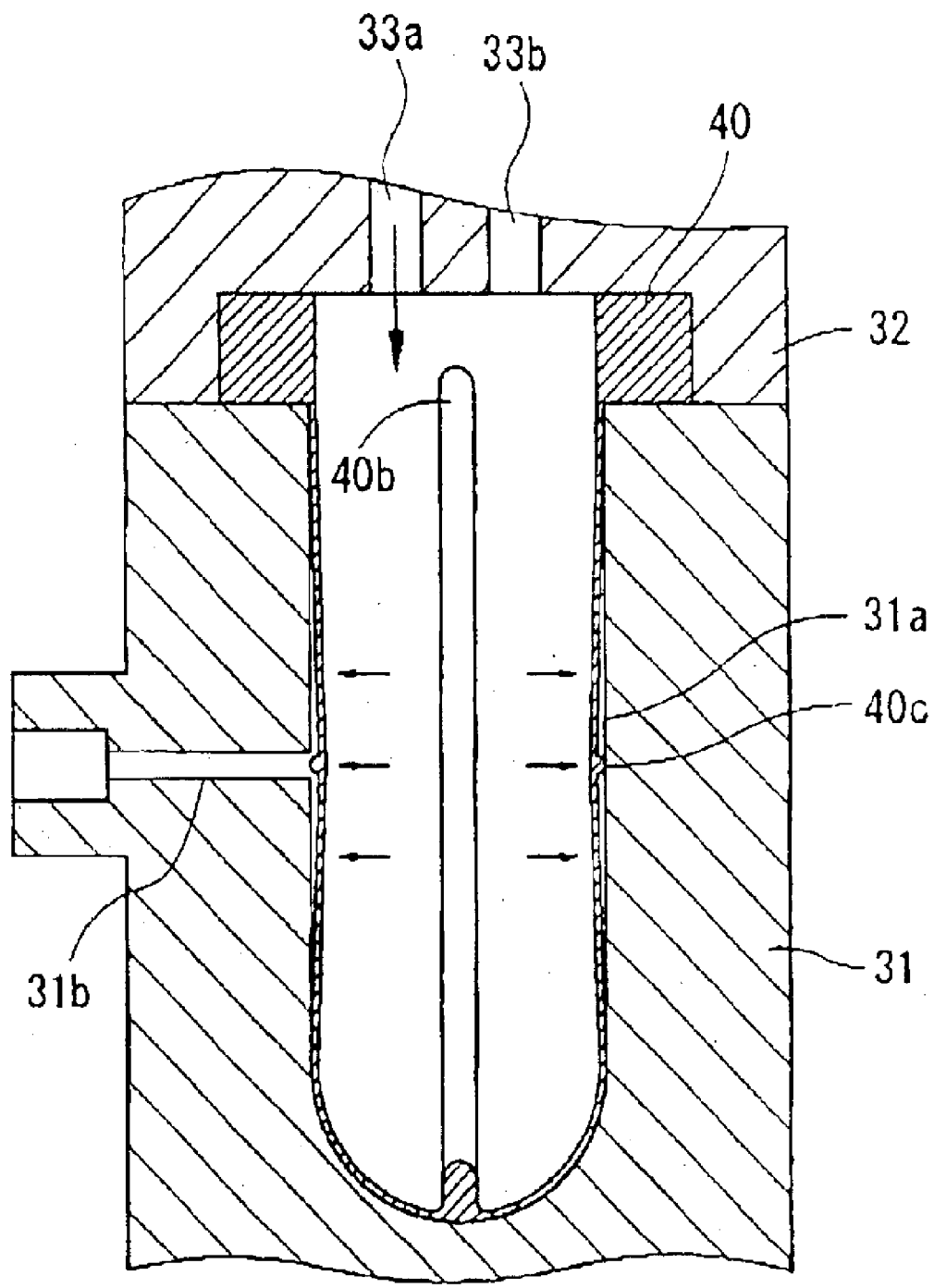
FIG. 6 is another sectional view of the diaphragm and the chamber.

Besides, since the rib 40c is provided around the circumference of the diaphragm 40, even if the diaphragm 40 is stored in a condition where the outside wall of the diaphragm 40 and the inside wall of the chamber 31a are approximately in contact with each other, there retained is a certain interstice (a space as a gas channel communicating with the pressure sensor 36) as shown in FIG. 6. For this reason, the sidewall of the diaphragm 40 does not lean to one side when altering its shape. Likewise, if the aspiration tube 16 is subjected to positive pressure, the sidewall of the diaphragm 40 may alter its shape so that the interstice disappears, and pressure increases in the space communicating with the chamber 31a. Therefore, pressure fluctuation toward positive pressure may be detected. Once the valve 18 has been opened, the irrigation liquid is led through the tube 15, the diaphragm 40 and the tube 19 to the aspiration tube 16 so that the aspiration pressure may recover to a reference state (0 mmHg: a state where no aspiration is performed). If it is intended that the aspiration pressure recover from the aspiration state to the reference state through opening the valve 18, knowing the pressure fluctuation toward positive pressure helps control the opening and closing of the valve 18 and makes it possible to stabilize the aspiration pressure in a steady state in a shorter time.

After the completion of the surgery, the unit 30 is removed from the connecting part 37, and the tubes used in the surgery may be thereby easily separated from the main body 1. In addition, since the diaphragm 40 helps the aspirated liquid running through the tubes be isolated from the aspiration pressure detecting system such as the pressure sensor 36 on the main body 1, the aspiration pressure may be accurately detected at all times while preventing the aspirated liquid from entering the apparatus. Since the aspirated liquid does not leak, recipients are free from infection due to the leak of the aspirated liquid. Moreover, the diaphragm 40 having a shape as described above may help broadly retain the shape-alteration in accordance with the pressure fluctuation and widen a range of the pressure to be detected, yet the diaphragm 40 is compact.

Figure 7:
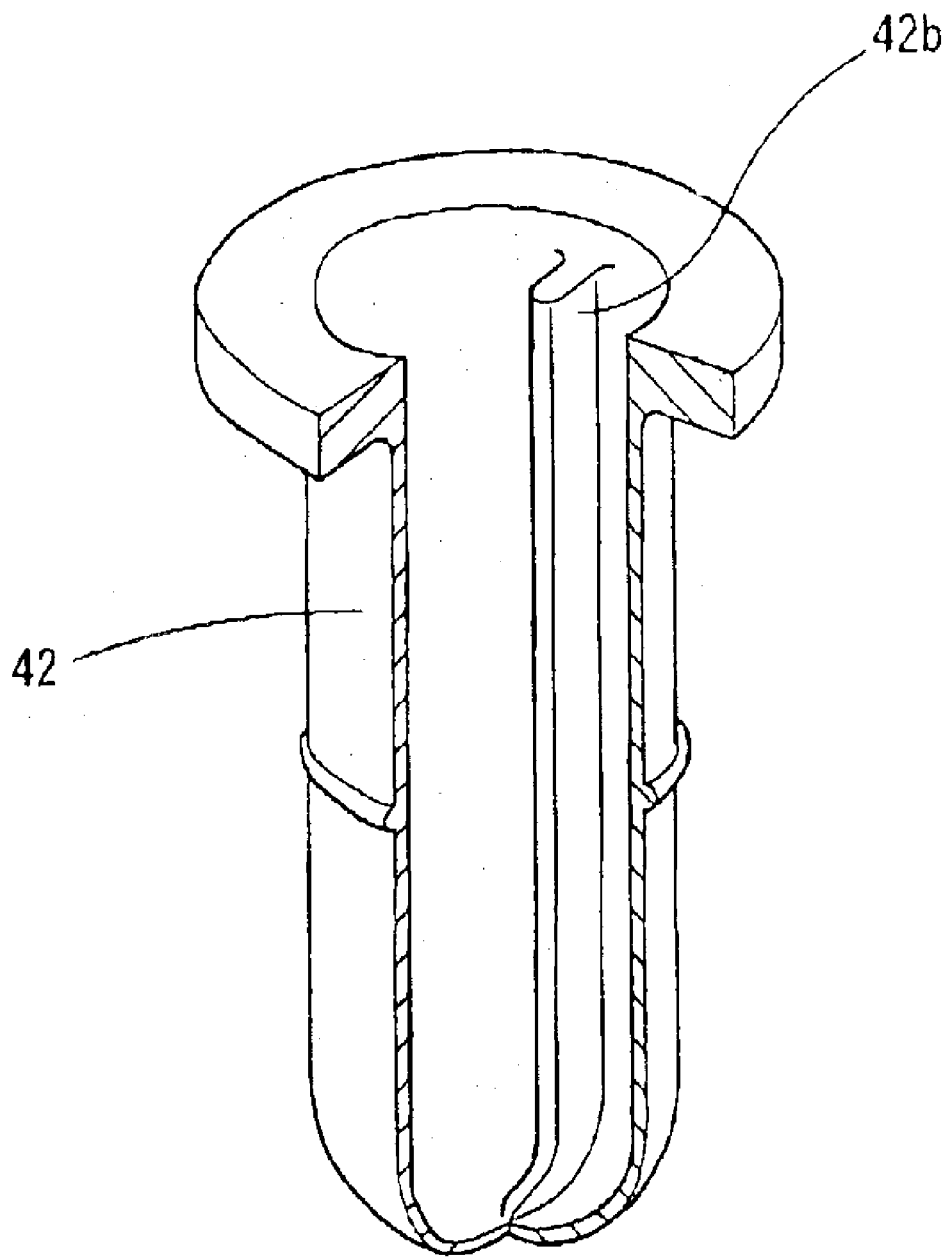
FIG. 7 is a view showing, a modified embodiment of the diaphragm.
Figure 8:
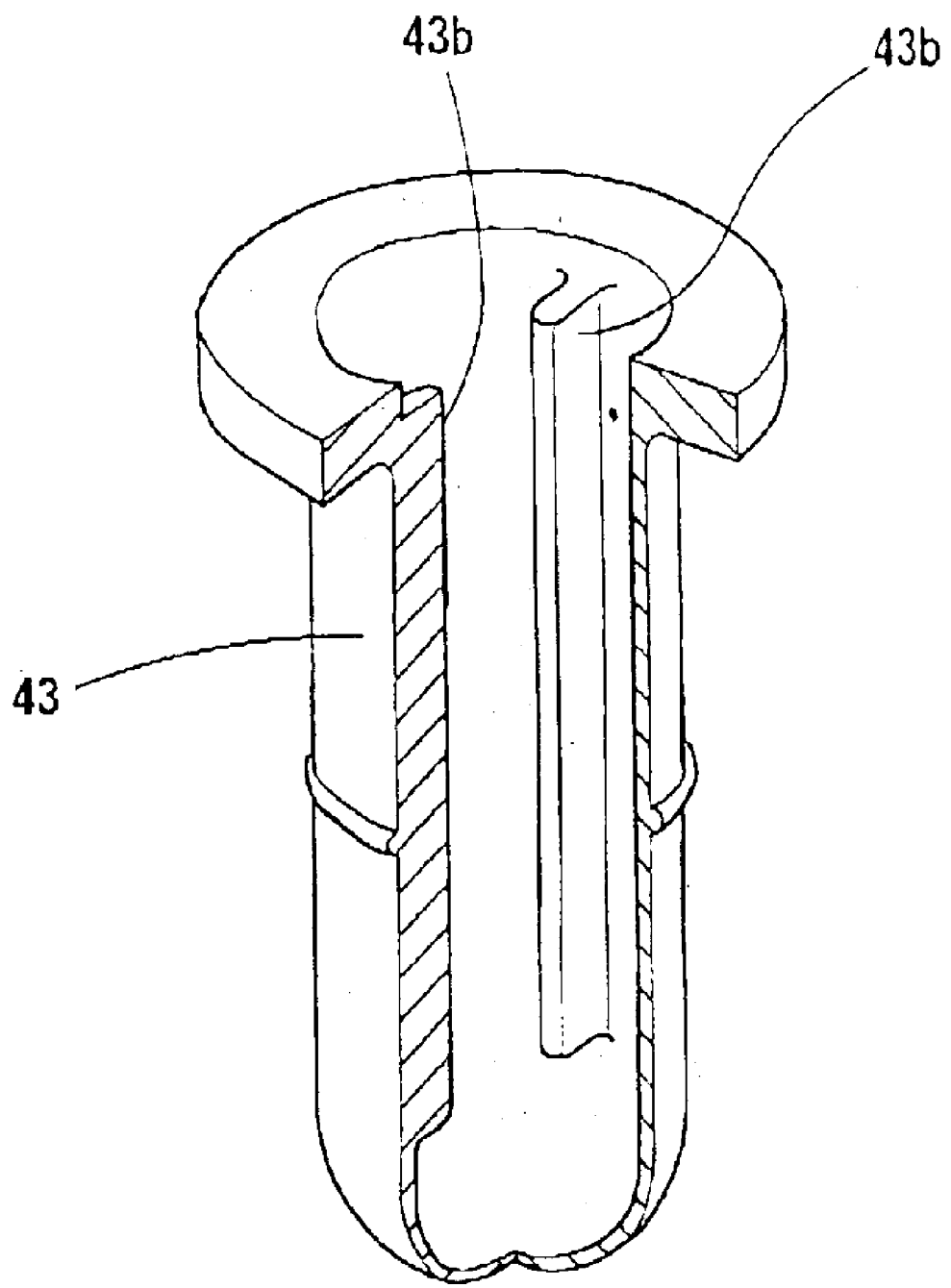
FIG. 8 is a view showing another modified embodiment of the diaphragm.

In the aforementioned configuration, the shape and number of the rib 40b for guiding the shape-alteration of the diaphragm 40 are not limited to those described above. For example, as shown in FIG. 7, a rib 42b may be provided on one side of a diaphragm 42. Besides, as shown in FIG. 8, ribs 43b of a diaphragm 43 may have a shape where the ribs 43b are partly removed in the bottom (on the peak side) of the diaphragm 43. Further, the two ribs 43b shown in FIG. 8 may have a shape in which their ends connect with each other. Furthermore, the connected rib 43b may have at least one hole on its sidewall.

Likewise, instead of using the ribs 40b and others, the unit 30 may be configured such that a sidewall of a diaphragm may be partly made hard, or such that a member having hardness such as a wire may be molded. Moreover, instead of forming a rib integrally with a diaphragm, a convex part may be provided on the upper case 32, which has the same shape as a rib of a diaphragm. In this case, a flexible diaphragm is arranged to cover the convex part.

In addition, for retaining a space as a gas channel between the inside wall of the chamber 31a and the outside wall of the diaphragm 40, a configuration may be applied where, instead of the rib 40c formed on the diaphragm 40, a slot which connects with the gas line 31b is provided on the inside wall of the chamber 31a so as to surround the diaphragm 40.

As described above, according to the present invention, the aspiration pressure may be accurately detected while the aspirated liquid is prevented from entering the apparatus. Moreover, the tubes may be easily connected with, and disconnected from the aspiration pressure detecting system, and there is no worry that the aspirated liquid could leak even when the tubes are removed.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An irrigation/aspiration apparatus which supplies an irrigation liquid to a surgical site and aspirates the supplied liquid with eliminated tissue to be discharged out of a body, the apparatus comprising:
   an aspiration channel;
   a shape-alterable diaphragm in pouch form, including a liquid chamber which communicates with the aspiration channel;
   a gas chamber which stores and surrounds the diaphragm; and
   a pressure sensor connecting with the gas chamber via a connecting part.

2. The irrigation/aspiration apparatus according to claim 1, further comprising guiding means for guiding shape-alteration of a sidewall of the diaphragm in accordance with pressure fluctuation applied to the aspiration channel.

3. The irrigation/aspiration apparatus according to claim 2, wherein the guiding means includes a rib provided on an inside wall of the diaphragm,
   wherein the rib extends in a direction of a depth of the diaphragm.

4. The irrigation/aspiration apparatus according to claim 1, further comprising interstice-retaining means for retaining an interstice between an inside wall of the gas chamber and an outside wall of the diaphragm.

5. The irrigation/aspiration apparatus according to claim 4, wherein the interstice-retaining means includes a rib provided on the outside wall of the diaphragm, wherein the rib extends in a direction of a circumference of the diaphragm.

6. An irrigation/aspiration apparatus which supplies an irrigation liquid to a surgical site and aspirates the supplied liquid with eliminated tissue to be discharged out of a body, the apparatus comprising:

an aspiration channel;

a shape-alterable diaphragm in pouch form, including a liquid chamber which communicates with the aspiration channel;

a gas chamber which stores and surrounds the diaphragm; and a pressure sensor connecting with the gas chamber via a connecting part, wherein a rib is provided on at least one of an inside wall and an outside wall of the diaphragm.

7. The irrigation/aspiration apparatus according to claim 6, wherein the rib is provided integrally with the diaphragm.

8. The irrigation/aspiration apparatus according to claim 6, wherein the rib is provided on the inside wall and the outside wall of the diaphragm, wherein the rib on the inside wall extends in a direction of a depth of the diaphragm and the rib on the outside wall extends in a direction of a circumference of the diaphragm.

* * * * *